Figure 1:
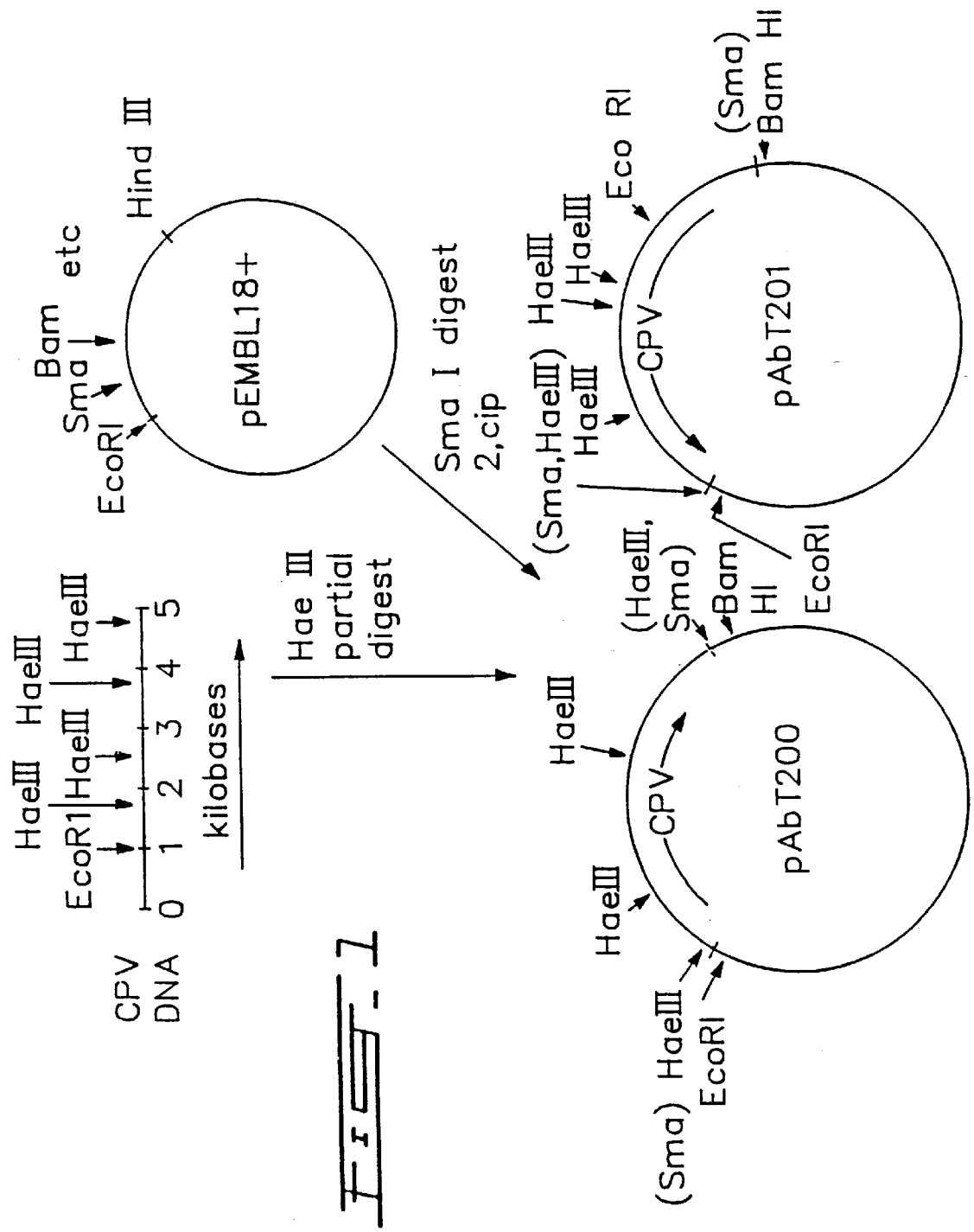

United States Patent [19]
Mazzara et al.

[11] Patent Number: 5,905,040
[45] Date of Patent: May 18, 1999

[54] PARVOVIRUS EMPTY CAPSIDS

[75] Inventors: Gail P. Mazzara, Winchester; Antonia T. Destree, Boston; Dennis L. Panicali, Acton, all of Mass.

[73] Assignee: Therion Biologics Corporation, Cambridge, Mass.

[21] Appl. No.: 07/657,156

[22] Filed: Feb. 15, 1991

Related U.S. Application Data

[62] Division of application No. 06/905,299, Sep. 8, 1986, abandoned.

[51] Int. Cl.⁶ .............................. C12N 15/00; C12N 7/00; C12N 5/00
[52] U.S. Cl. ..................................... 435/320.1; 435/235.1; 435/325; 435/455
[58] Field of Search ................................. 435/69.1, 70.1, 435/70.3, 320.1, 235.1, 325, 455; 935/32, 57

[56] References Cited

FOREIGN PATENT DOCUMENTS

| | | |
|---|---|---|
| 0 117 063 | 8/1984 | European Pat. Off. . |
| 0 117 767 | 9/1984 | European Pat. Off. . |
| 0 199 480 | 10/1986 | European Pat. Off. . |
| 0 238 893 | 9/1987 | European Pat. Off. . |
| WO90/05538 | 5/1990 | WIPO . |

OTHER PUBLICATIONS

Pintel et. al. (1984) J. Virol. 52, 320–327.
Rhode (1985) J. Virol. 54, 630–633.
Labieniec–Pintel, Journal of Virology, 57(3):1163–1167 (1986).
Parrish, Archives in Virology, 72:267–278 (1982).
Parrish and Carmichael, Virology, 129:401–414 (1983).
Parrish, et al., Science, 230:1046–1049 (1985).
Law, et al., Molecular and Cellular Biology, 3(11):2110–2115 (1983).
Pintel, et al., Journal of Virology, 52(2):320–327 (1984).
Ramabhadran, et al., Gene, 38:111–118 (1985).
Rhode, et al., Chemical Abstracts, 103:136207a (1985).
Carlson, et al., Biological Abstracts, 80:100811 (1985).
Grubman, et al., Journal of Virology, 56(1):120–126 (1985).
Shih, et al., Proc. Natl. Acad. Sci. USA 75(12):5807–5811 (1978).
Valenzuela, et al., "Synthesis and Assembly of Hepatitis B Virus Antigens in Heterologous Systems" in Hepatitis B, The Virus, The Disease and The Vaccine, Ed. Millman, et al., Plenum Press, NY, pp. 225–236 (1984).
Valenzuela, et al., Nature, 298:347–350 (1982).

*Primary Examiner*—Deborah Crouch
*Attorney, Agent, or Firm*—Ronald I. Eisenstein; David S. Resnick; Sewall P. Bronstein

[57] ABSTRACT

Empty viral capsids, particularly animal parvoviral empty capsids, induce protective antibody response against the virus. The empty viral capsids are obtained by recombinant DNA techniques. Expression vectors are constructed containing structural genes encoding capsid proteins in self assembling form. Eukaryotic transfectants express self-assembled empty viral capsids which can be used to vaccinate against the virus or antigenically related species of the virus.

15 Claims, 6 Drawing Sheets

PARVOVIRUS EMPTY CAPSIDS

CROSS REFERENCE TO RELATED APPLICATIONS

The present Application is a Divisional Application of U.S. Ser. No. 06/905,299; filed Sep. 8, 1986 (now abandoned).

BACKGROUND

The autonomously replicating parvoviruses, which include canine parvovirus, mink enteritis virus, feline panleukopenia virus, and other porcine, bovine, rodent, and human parvoviruses, are among the smallest known DNA viruses. Infectious virions are spherical, non-enveloped particles 20–25 nm in diameter that contain three species of structural polypeptide, VP1, VP2', and VP2, with overlapping amino acid sequences. The genome of these viruses consists of a predominantly single-stranded, linear DNA molecule with a molecular weight of $1.35$–$1.70 \times 10^6$ (approximately 5000 nucleotides in length). This DNA encodes a noncapsid protein (NTCVP1) in the 3' (left-hand) portion of the genome, as well as the major capsid proteins, which are encoded by overlapping regions of viral DNA in the 5' (right-hand) portion of the genome.

Canine parvovirus (CPV) was first recognized as the etiological agent responsible for a series of disease syndromes in dogs in 1978. There is no serological evidence prior to 1978 to indicate existence of the virus before that time. It is believed that CPV arose from a single source around that time. The virus has rapidly spread to pandemic proportions. CPV is genetically and antigenically related to feline panleukopenia virus (FPV), mink enteritis (MEV) and other parvoviruses which cause disease in animals. It is believed that CPV is a host range variant (mutant) of one of these viruses, most likely FPV, since FPV modified live vaccines were and are widely used.

There are two types of parvovirus vaccines currently in use: a modified live virus vaccine and a killed whole virus vaccine. While effective these vaccine preparations have several drawbacks. Modified live virus has the potential for reversion to a virulent form. In addition, continuous use of these live virus vaccines presents the risk that the virus will mutate to develop a wider host range. Further, the ability of modified live virus vaccines to induce protection can be inhibited by maternal antibodies which prevent replication of the modified virus in newborn animals often the time of greatest susceptibility to disease.

Killed virus vaccines do not revert to virulent forms and they are capable of stimulating immunity in the presence of maternal antibodies. However, killed virus preparations are generally less immunogenic and evoke lower antibody titers than live virus preparations. One reason for this is that the procedures for inactivating the virus cause denaturation of viral protein. In addition, killed viruses do not replicate in the vaccinated animal. In order to compensate for this immunogenic deficiency, high doses of killed virus must be given. But, the administration of high doses of protein may cause complications, such as anaphylatic shock; furthermore it can be expensive to produce large quantities of inactivated virus preparations.

CPV, FPLV, and MEV are very closely related, both genetically and serologically. CPV isolates from nature replicate efficiently in dogs and in cat or dog monolayer cell cultures. FPV isolates grow in cats and in cat monolayer cell cultures, but not in dog monolayer cell cultures. Both viruses replicate to a limited extent in the alternate animal host. As a consequence of the similar antigenic structures of these parvoviruses, vaccination with any one of these viruses can produce cross-species protective immunity; thus, both modified live and killed FPV vaccines have been used to protect dogs against canine parvovirus infection, and modified live or killed CPV vaccines have been used to protect minks from mink enteritis, and should elicit protective immunity to FPLV as well.

It has been previously demonstrated that empty capsids of a murine parvovirus, the Minute Virus of mice (MVM) could be produced by recombinant DNA techniques (Pintel et al. *J. Virol.* 52, 320 (1984)). In those experiments, recombinant plasmids containing the genomes of both bovine papillomavirus type I and MVM were used to transform mouse C127 cells, a natural permissive host for MVM infection. Cells harboring these plasmids could, however, be selected only by their transformed morphology; the dependence on this morphological change as the selective marker for cells harboring the BPV-derived plasmid limits the host range for the use of these plasmids to those cells which display the transformed phenotype, including mouse cell lines C127 and NIH 3T3.

The purpose of the experiments described in the previous paragraph was to generate superinfectible host cell lines which constitutively express MVM gene products as a tool for the study of MVM gene expression. During the course of analysis of the MVM/BPV transformed cell lines, it was noted that the viral proteins VP1 and VP2' assemble into empty virion particles.

SUMMARY OF THE INVENTION

This invention pertains to vaccines based upon immunogenic empty viral capsids, i.e. intact viral capsids which contain no viral genetic material; to methods of preparing the immunogenic empty viral capsids; and to methods of vaccination employing the capsids. The invention is based upon the discovery that immunogenic, empty capsids of canine parvovirus (CPV) can be produced by genetically transformed eukaryotic cells and that the capsids so produced elicit a protective immune response against the parvovirus and antigenically related parvoviruses.

The method of this invention for production of canine paroviral empty capsids can be employed to produce empty capsids of other types of parvoviruses including feline, mink, porcine, bovine, and human parvoviruses. Further, the techniques are applicable to other classes of DNA viruses, such as poliovirus, which have relatively simple capsid structures which are capable of self-assembly in a eukaryotic host.

According to the method of this invention, immunogenic empty viral capsids are expressed in eukaryotic host cells by transfecting the cells with expression vectors capable of expressing the protein constituents of the capsids. Essentially, the expression vector comprises the structural genes encoding the capsid proteins of interest under the control of a eukaryotic promoter, genetic elements for replication in a eukaryotic host and a gene or genes which allow selection of eukaryotes transfected with the vector. In preferred form, the vector includes an origin of replication for a bacterial host (allowing the vector to be amplified in a bacterial cloning system) and genetic elements which provide for episomal replication in the eukaryotic host (allowing amplification of expression of the capsids in the host). Eukaryotic cells transformed with the expression vectors of this invention express capsid proteins which self-assemble into immunogenic empty viral capsids.

Empty capsids of CPV were produced by the following recombinant DNA techniques. The region of the CPV genome which contains the structural genes encoding the CPV capsid proteins VP1 and VP2' was cloned from viral RF (replication form) DNA. DNA fragments with or without the endogenous CPV transcriptional promoter were then inserted at different sites in a bovine papillomavirus vector containing the antibiotic selectable marker $neo^R$ (neomycin phosphotransferase), which confers resistance to the antibiotic G418 in eukaryotic cells, and these chimeric vectors were used to transfect mouse 3T3 and C127 cells and a dog cell line designated A72. Cell lines containing the vectors were selected by G418 resistance and assayed for expression of CPV proteins. A number of eukaryotic cell lines were generated which express VP1 and VP2' proteins which self-assemble into empty capsids as determined by their ability to hemagglutinate red blood cells, and by a variety of chemical and physical parameters.

The empty CPV capsids exhibited antigenic epitopes identical to intact wild type CPV, as determined with a bank of monoclonal antibodies. The empty capsids were tested for immunogenic potential in dogs and they were capable of eliciting CPV specific antibodies which can inhibit RBC hemeagglutination (hemagglutination inhibition). Subsequent challenge experiments in dogs demonstrated that the empty capsids were capable of protecting dogs against CPV induced disease.

Vaccines based upon empty viral capsids offer several advantages over live modified and killed virus vaccines. Because the empty capsids lack viral genetic material the risk of reversion to virulence is eliminated. In addition, the empty capsids are constituted of protein in native form and thus the capsids should be more immunogenic than killed virus.

Empty viral capsids can also be used diagostically. For example, an empty viral capsid can be employed as antigen for detection of antiviral antibody in a sample bodily fluid. The capsids can also be used to raise antibody against the virus for use in detecting the presence of virus in a bodily fluid sample.

BRIEF DESCRIPTION OF THE DRAWINGS

FIG. 1 shows the steps involved in the cloning of CPV DNA sequences into the prokaryotic vector pEMBL18+.

FIG. 2 shows the recombinant retroviral vector DOL with inserted CPV DINA sequences (pAbT 210).

FIG. 3 shows the derivation of the plasmid vector, pdMMT$neo^R$ (pAbT230). This plasmid served as a precursor for production of plasmids pAbT241, pAbT243 and pAbT245, which are all DNA vectors capable of expressing self assembling canine parvoviral capsids in eukaryotic hosts.

FIG. 4 shows the construction of the recombinant CPV/BPV plasmid pAbT241

FIG. 5 shows the construction of the recombinant CPV/BPV plasmid pAbT243

FIG. 6 shows the construction of the recombinant CPV/BPV plasmid pAbT245

DETAILED DESCRIPTION OF THE INVENTION

The expression of empty viral capsids and the preparation of vaccine compositions containing the capsids is detailed below. Particular reference is given to one context in which preferred embodiments of the invention find application, i.e., the expression of empty capsids of canine parvovirus and use of such capsids for vaccination against canine parvovirus and antigenically related parvoviruses. As mentioned, the techniques described are applicable to production of empty capsids of other members of the parvovirus family, including feline, mink, porcine, bovine and human parvoviruses. Moreover, these techniques are applicable to viruses, including both DNA and RNA viruses, which are characterized by relatively simple virion particles containing one or a few structural proteins assembled into a capsid which contains the viral nucleic acid and non-structural proteins. Examples of such viruses include Tabaco Mosaic Virus (one structural protein), Poliovirus (4 structural proteins), Reovirus (3 structural proteins) and Parvovirus (2–3 structural proteins). For these simple viruses, it may be possible, using the recombinant DNA techniques described herein, to express all of the viral structural proteins in an appropriately designed expression system consisting of eukaryotic or prokaryotic expression vector in a suitable host cell. As in the case of canine parvovirus, viral structural proteins expressed by genetic transformation of a host cell line can spontaneously assemble into empty capsid particles devoid of viral nucleic acids and non-structural proteins. These non-infectious particles, which may closely resemble authentic virions, would then be capable of stimulating the same or similar immunogenic response as does the infectious virus from which they are derived. Such empty capsids would be useful in the formulation of an anti-viral vaccine; they could also be used as a basis for the development of diagnostic reagents.

The methodology for production of empty capsids is discussed in five separate sections. In the first section, methods for obtaining genes encoding viral capsid proteins in self-assembling form are addressed. The second section deals with the construction of expression vectors for expression of the empty capsids. In the third section, appropriate eukaryotic host cells for capsid expression and procedures for transforming the cells with the expression vectors are described. In the fourth section the preparation of vaccine compositions containing the capsids and the use of these compositions for vaccination are discussed. The fifth section is devoted to the diagnostic uses of the empty viral capsids.

1. Preparation of genes encoding viral capsid proteins.

Genes encoding capsid proteins in self-assembling form can be obtained from genomic DNA of the virus for which empty capsids are to be prepared. The viral DNA can be isolated by standard techniques for isolation of viral DNA from the desired virus. A particularly preferred technique for isolation of CPV DNA, for example, is described by McMaster et al. *J. Virology* 38, 317 (1981), the teachings of which are incorporated by reference herein.

The viral genes encoding capsid proteins in self-assembling form can be obtained by cleaving the isolated genomic or subgenomic DNA into fragments which contain the desired genes. The object is to obtain a fragment or fragments of the genome which contain gene(s) encoding the capsid protein(s) in a form which will self-assemble into capsids within the eventual eukaryotic transformant. Generally, the fragments will contain the entire structural genes encoding each capsid constituent necessary for self-assembly intracellularly. In addition, depending upon the design of the expression vector (as described in more detail below) fragments of viral genomic DNA can be made to include the viral transcriptional promoter for the genes encoding the capsid proteins.

DNA fragments of the viral genome can be obtained by enzymatic cleavage with restriction endonucleases. If restriction enzyme maps of the viral genomic DNA are available, the appropriate enzyme(s) can be chosen to yield desired fragments containing the capsid genes by reference to the map. In other cases, appropriate enzymes and conditions of digestion may be determined experimentally.

A preferred restriction endonuclease for cleavage of CPV DNA, for example, is HaeIII. Partial digestion of CPV DNA with this restriction endonuclease yields several fragments of CPV DNA, at least one of which contains the VP1 and VP2' genes with the endogenous CPV promoter for these genes. Other restriction endonucleases may be used to provide appropriate CPV DNA fragments containing the genes encoding self-assembling CPV capsid proteins with or without the CPV promoter.

DNA fragment(s) encoding the capsid protein(s) can be amplified by cloning the fragment into a bacterial host. For this purpose various cloning vectors can be used. Examples are plasmids pBR322 and pEMBL.

The genes encoding the capsid protein can then be used to construct an expression vector for the viral capsid according to the methodology described in the next section.

The specific procedure employed to obtain the genes encoding the CPV capsid proteins VP1 and VP2' is depicted in FIG. 1. CPV DNA was partially digested with the restriction endonuclease HaeIII. The fragments produced by the partial digestion were inserted into the plasmid pEMBL18+, an E. coli cloning vector, at the single SmaI site of the plasmid. E. coli cells were transformed by the recombinant plasmids and transformed cells were selected for the presence of plasmids containing the desired CPV DNA fragments by hybridization techniques. Two recombinant plasmids designated pAbT200 and pAbT201 were selected. pAbT200, which carries approximately 64% of the CPV genome, contains the structural genes for the VP1 and VP2' genes along with their transcriptional promoter. pAbT201 contains approximately 95% of the CPV genome, including the structural genes for VP1 and VP2' and their endogenous promoter.

Figure 2:
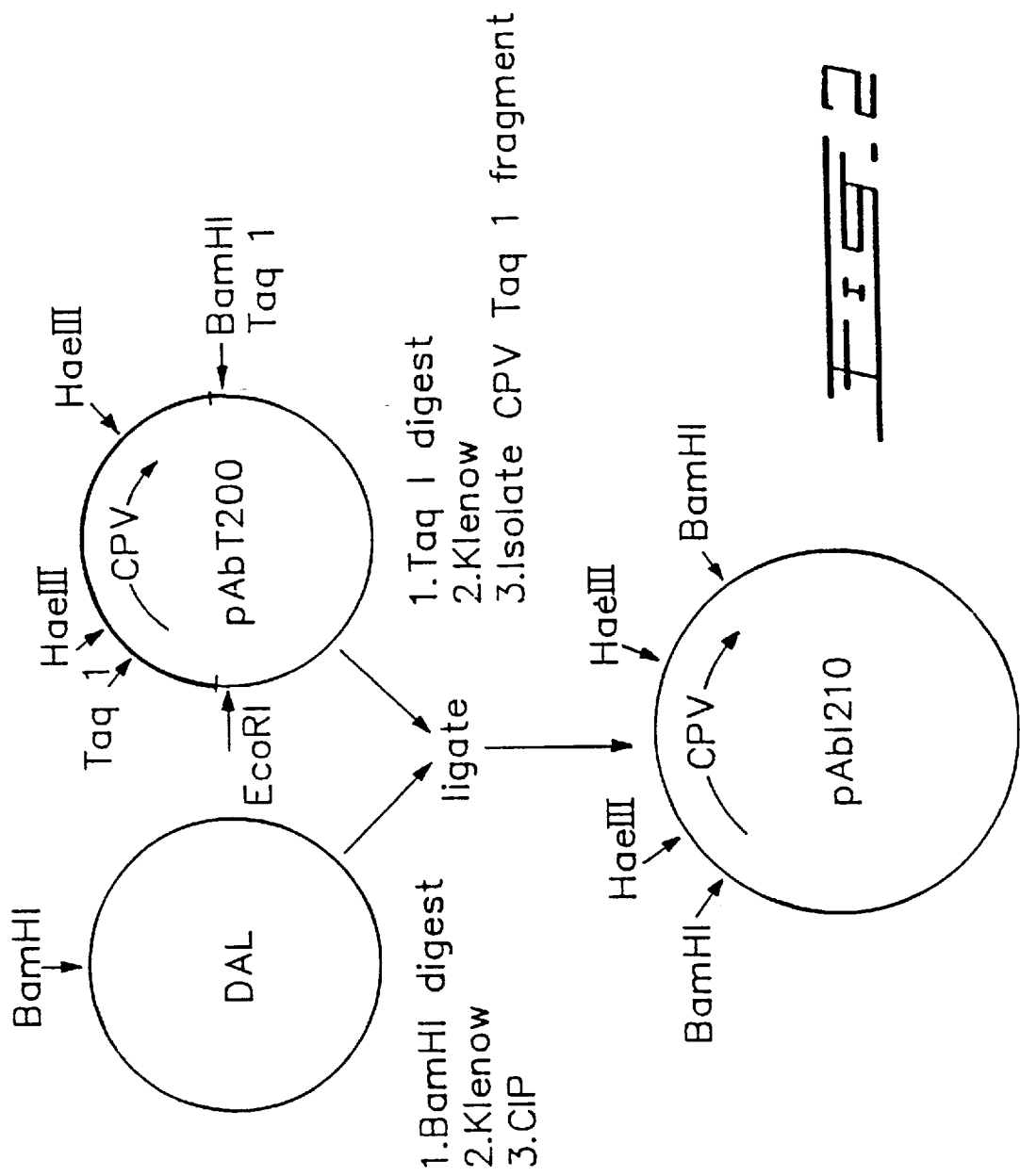
Figure 3:
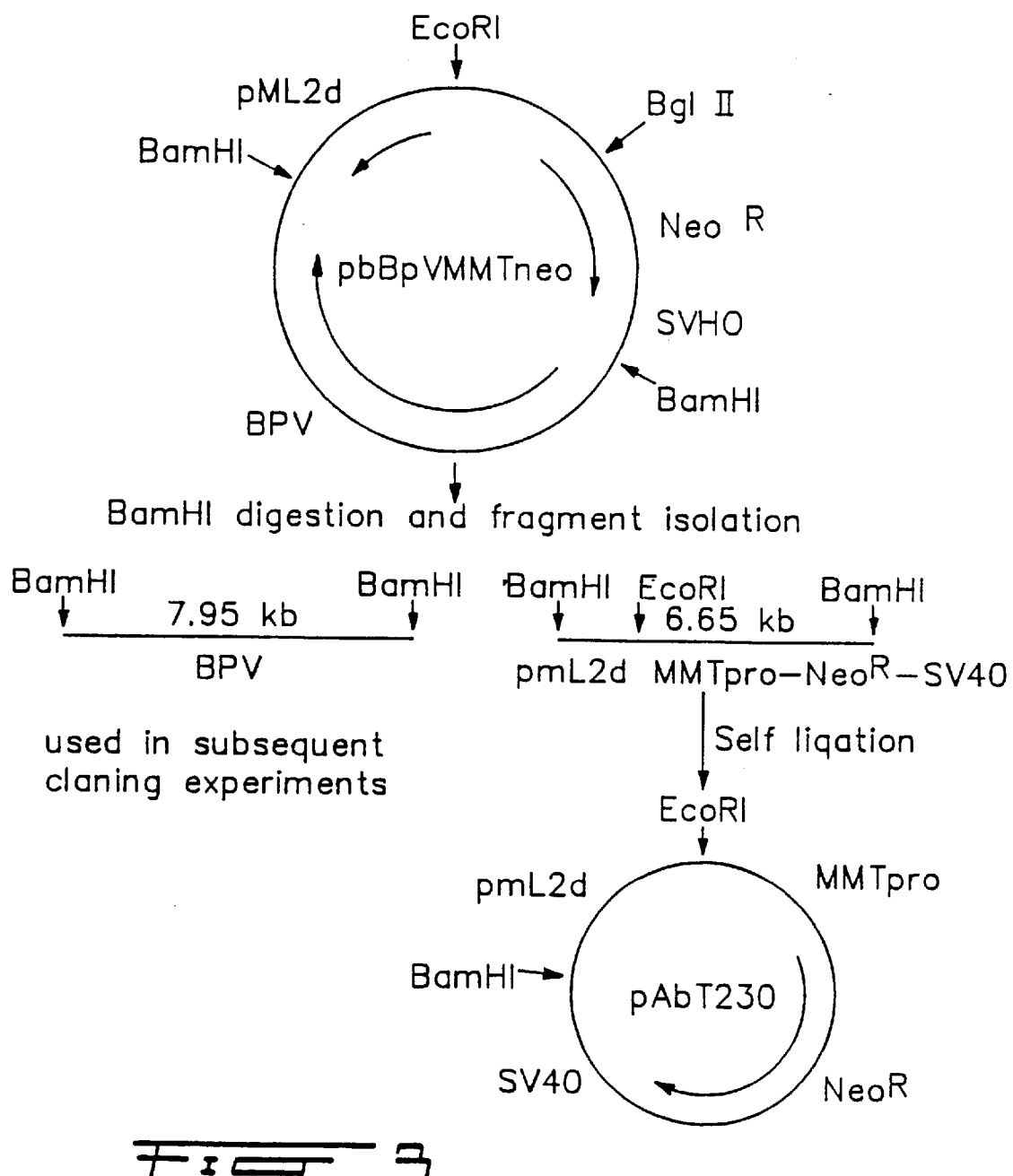

As schematically depicted in FIG. 2, the fragment harbored by pAbT200 was cloned into a DOL vector to yield a CPV fragment carrying the VP1 and VP2' genes absent their endogenous promotor and flanked at either end by BamHI restriction sites. The resulting plasmid, pAbT210, served as a convenient source of this CPV fragment, which could be readily excised and cloned into compatible restriction sites by virtue of its flanking BamHI restriction sites. Plasmids other than DOL which harbor a unique BamHI site, such as pBR322 or pEMBL18+, could have been used to obtain the CPV fragment in this form i.e., with flanking BamHI ends.

2. Construction of Expression vectors for expression of empty viral capsids.

Expression vectors capable of replication and expression of the genes encoding the capsid proteins can be constructed by assembling the capsid genes in conjunction with a eukaryotic promoter in a vector capable of replication in a eukaryotic host and having a selectable marker which allows selection of host cells transformed with the vector. Thus, in general, a chimeric expression vector for capsid expression will contain the capsid genes of interest under direction of an endogenous or exogeneous eukaryotic promoter, the genetic material necessary for replication in a eukaryotic host and a gene or genes which confer a selectable phenotypic trait upon the host cell.

It is particularly advantageous to construct expression vectors which can replicate in a bacterial host as well as replicate and function in eukaryotic host. With such dual capacity the chimeric expression vector can be amplified in a convenient bacterial cloning system to provide ample amounts of the expression vector for transfection of the eukaryotic host. Accordingly, a preferred expression vector for expression of immunogenic empty viral capsids in a eukaryotic host cell will contain the following elements:

a. prokaryote derived origin of relication (which permits replication of the vector in a bacterial host cell);

b. a eukaryotic genetic element which permits replication in a eukaryotic host;

c. a eukaryotic promoter (which can direct expression of the genes encoding capsid protein in a eukaryotic host cell); and d. genes encoding the capsid protein (under the direction of the eukaryotic promoter).

The bacterial origin of replication can be obtained from any bacterial plasmid, for example, pBR322, pUC, pEMBL type plasmids or other prokaryotic origins of replication. Eukaryotic elements for replication can be derived BPV, SV40, or other sources. Eukaryotic promoters can be the murine metallothionein promoter, the SV 40 early promoter, heat shock gene promoter or other exogenous eukaryotic promoters, or, as discussed, the endogenous viral promoter (s) for the capsid encoding genes.

As mentioned, the expression vector should include markers for selection of eukaryotic host cells transformed with the vector. In addition, the vector should contain a marker for selection of prokaryotic transformants. For selection in prokaryotic cells, traditional markers such as genes conferring antibiotic resistance can be incorporated into the vector along with necessary regulatory elements for these genes. These include the genes for ampicillin, kanamycin or tetracycline resistance.

For selection in eukaryotes, several different types of markers can be used. One such marker is the genome, or at least the transforming portion of the genome, of bovine papilloma virus. The BPV genome allows selection of transfected murine cells by virtue of the transforming properties of the BPV DNA. Cells which have taken BPV DNA into their nuclei can become transformed. A feature of the transformed phenotype is the loss of contact inhibition, which allows identification of these transformed cells as foci of replicating cells. These foci can then be isolated and grown as a homogeneous population of cells. This selection procedure is limited, however, to a few murine cell lines. A more general selection procedure is provided by the neo$^R$ (neomycin phosphotransferase) gene. Most eukaryotic cells are sensitive to the antibiotic geneticin (G418) which inhibits protein synthesis. If a neo$^R$ gene is taken into a cell and expressed within that cell it is possible to preferentially select cells in the presence of G418, an analog of neomycin which is readily taken up by eukaryotic cells (Jiminiz et al., Nature 287, 869 (1980)).

Another selectable marker for selection of eukaryotic transfectants is the xanthine-guanine phosphoribosyl transferase gene, designated gpt. Selection with gpt is based on the ability of the enzyme encoded by this gene to use xanthine as a substrate for purine neucleotide sysnthesis; the analogous endogenous enzyme cannot. In a culture medium containing xanthine and mycophenolic acid which blocks the conversion of inosine monophosphate to xanthine monophosphate, only cells expressing the gpt gene can survive.

Particularly preferred vectors are capable of replicating as multicopy, non-integrated circular plasmids within the eukaryotic host cell. This episomal replication provides in effect a type of gene amplification and consequently a subsequent amplification of gene expression. This capability for episomal replication can be conferred by, for example, the BPV genome.

Figure 4:
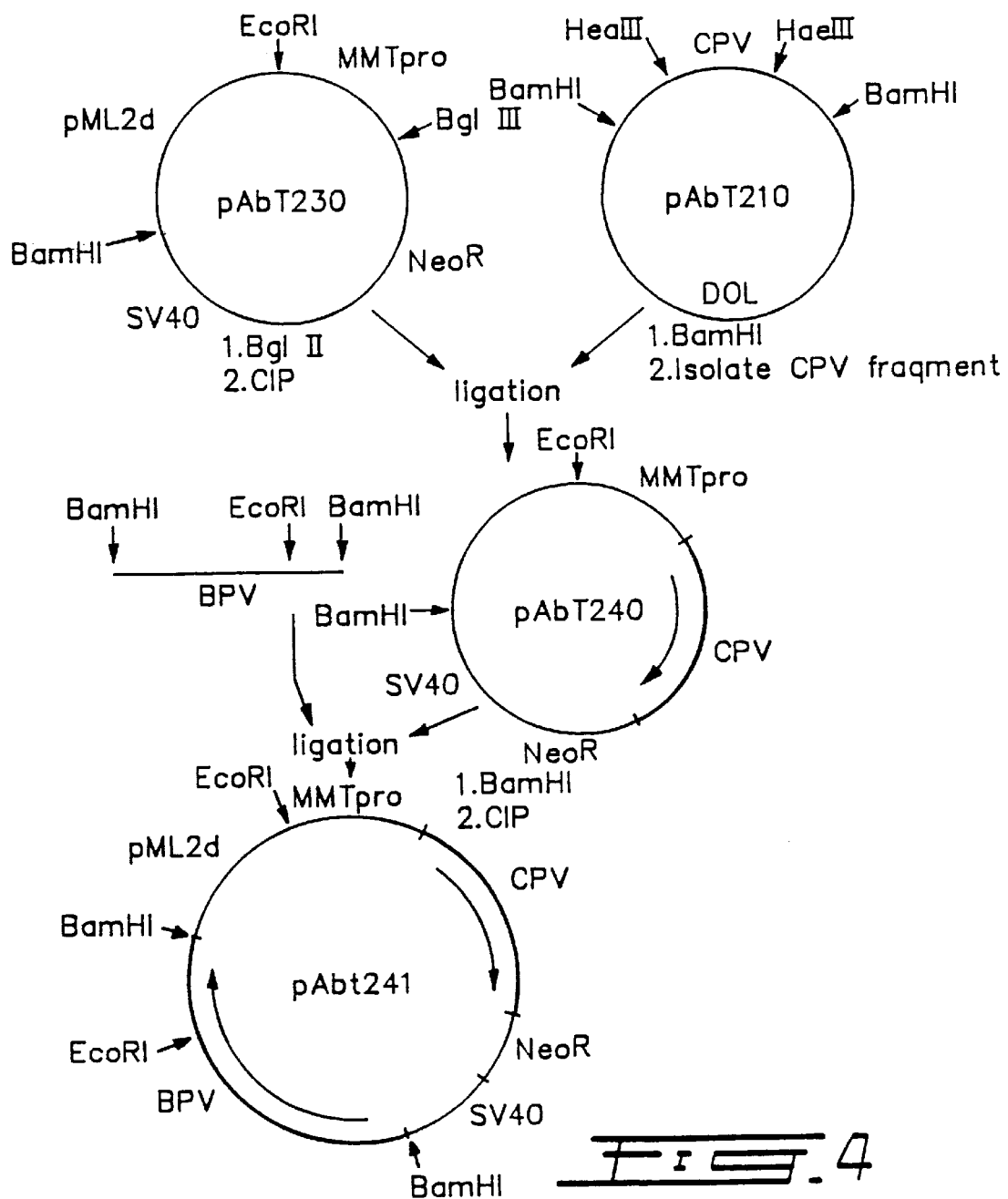

Along the lines discussed above, three chimeric expression vectors for expression of CPV empty capsids designated pAbT241, pAbT243 and pAbT245 were constructed. The expression vector pAbT241 (shown schematically in FIG. 4) contains the following elements:

a. a pBR322-derived origin of replication;
b. the eukaryotic MMT promoter
c. structurual genes encoding CPV capsid proteins VP1 and VP2;
d. the entire BPV genome and the $neo^R$ gene; and e. SV40 derived transcriptional regulatory elements.

In this vector, the MMT promoter is located just upstream of the VP1 and VP2' genes so that the genes are under the direction of this promoter. The $neo^R$ gene is disposed just downstream of the VP1 and VP2 genes so that it too is under control of the MMT promoter.

The expression vector pAbT243 (shown schematically in FIG. 5) contains the same elements as pAbT241 but in different arrangement. In addition, it contains the endogenous CPV transcriptional promoter for the VP1 and VP2' genes. The CPV promoter and VP1 and VP2' genes are located upstream of the MMT promoter. The MMT promoter is located adjacent to the $neo^R$ gene and controls transcription of this gene.

The expression vector pAbT245 is similar to pAbT243 except that the location of the VP1 and VP2' genes and their promoter adjoins the BPV genome.

The chimeric expression vectors were constructed by inserting the CPV DNA into a precursor plasmid (AbT230) formed by removal of the BPV genome from the plasmid $pdBPVMMTneo^R$ (See FIG. 3). pAbt230 contains the MMT promoter and the $neo^R$ gene. To construct pAbT241, CPV DNA was excised from the DOL vector by BamHI digestion and inserted into a BglII site of pAbT230 just downstream of the MMT promoter to yield an intermediate contruct designated pAbT240. The BPV genome was then incorporated at the BamHI site of this intermediate vector to produce pAbT241.

pAbT243 was constructed by excising CPV DNA from pAbT201 by EcoRI digestion and inserting the resulting CPV fragment into the EcoRI site of pAbT230. The BPV genome was then inserted as was done for pAbT241.

pAbT245 was constructed by excising CPV DNA from pAbT201 by EcoRI digestion and inserting the fragment into the BamHI site of pAbT230 with BamHI linker. The BPV genome was then inserted at one of the two BamHI sites.

The plasmids pAbT241, pAbT243 and pAbT245 have been deposited at the American Type Culture Collection in Rockville, Md. and have been assigned the following accession numbers:

| plasmid | accession # |
|---|---|
| pAbT241 | 67194 |
| pAbT243 | 67195 |
| pAbT245 | 67196 |

3. Host Cells and Transfection Procedures

In order to produce empty capsids, it is necessary to introduce the chimeric expression vector into appropriate host cells for expression of viral structural proteins. Eukaryotic host cells for expression of empty viral capsids are selected on the basis of a number of factors as described in the following.

A. The appropriate host cell should be compatible with the transfection system

Eukaryotic host cells must be transfectable by one of the conventional transfection techniques, such as the calcium-phosphate precipitation method described in this disclosure. Other transfection techniques include the use of DEAE-dextran, electroporation, or protoplast fusion.

Many cell lines can be transfected by one or more of the above techniques. These include (but are not limited to) NIH 3T3 cells, canine A72 cells, chinese hamster ovary (CHO) cells, CV-1 cells, BSC40 cells, chick embryo fibroblasts and others well known in the art.

B. The appropriate host cell must be compatible with the selection system used to detect cells transformed with the expression vector.

A variety of techniques are available for selecting transformed cells. The preferred system is that of selection for expression of the $neo^R$ gene, which renders transformed cells resistant to G418. A variety of other selection systems, well known in the art, can be incorporated into the expression vector/host cell system; these include thymidine kinase (TK) selection in TK-host cells; the xanthine-guanine phosphoribosyl transferase (gpt) system, mentioned previously, which requires host cells deficient in gpt; and selection for the transformed phenotype conferred by the BPV genome, which is limited to certain murine cell lines. Selection for empty capsid production can be done by hemagglutination assay which measures the ability of the expressed CPV product to hemagglutinate red blood cells, a property possessed only be intact capsids, and not by the individual viral proteins; and by other chemical or biological techniques including direct visualization of capsids by electron microscopy and characterization by CsCl gradient centrifugation.

C. The optimum host cell for capsid production should be capable of continuous cell culture.

Many established enkaryotic cell lines are capable of continuous propagation in culture. Some examples are NIH 3T3 cells, L cells, canine A72 cells, chinese hamster ovary cells and Vero cells. Primary cells derived from various species can also be used.

D. Host cell lines should be certified for use in the production of vaccines by the appropriate regulatory agencies.

As an example, the United States Department of Agriculture (USDA) has certified certain cell lines for use in producing parvovirus vaccines for animals. These include the carandal cell line (derived from feline kidney) and a canine cell line, madin-Darby canine kidney cells. Other cell lines have been certified by the Federal Drug Administration for use in producing human vaccines.

It is important to use an antibiotic selection system for transforming these cell lines, since they are not deficient in certain of the enzymes commonly used for selection such as gPt and TK.

4. Vaccine Preparation

Vaccine compositions for vaccination against the virus from which the empty capsids are derived generally comprise an immunizing amount of the empty viral capsid in a pharmaceutically acceptable vehicle. For example, such vaccines can be prepared as injectables, e.g., liquid solutions or suspensions. Solid forms for solution in, or suspension in, a liquid before injection also can be prepared. Optionally, the preparation also can be emulsified. The active antigenic capsids can be mixed with excipients which are pharmaceutically acceptable and compatible with the active capsids. Examples of suitable excipients are water, saline, dextrose, glycerol, ethanol, or the like, and combinations thereof. In addition, if desired, the vaccine can contain minor amounts of auxiliary substances such as wetting or emulifying agents, pH buffering agents, or adjuvants, such as aluminum hydroxide, which enhance the effectiveness of the vaccine. The vaccines are conventionally administered parenterally, by injection, for example, either subcutaneously or intramuscularly.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to the subject. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

The empty viral capsids can be obtained from the producing transformed cells in the form of whole cell lysates or they can be purified by differential centrifugation, ultrafiltration or other conventional techniques for protein purification. The preferred form for parvovirus vaccines is the whole-cell lysate; these preparations can be lyophilized and reconstituted.

The immunizing dosage of empty capsids may be determined experimentally for each species of parvovirus capsid and for individual preparation of empty capsids. This may be done by titrating the dosage of empty capsids, as measured in hemagglutination (HA) units, in the appropriate host animal (e.g. CPV in dogs, cats or mink) and subsequent measurement of the immunological response to viral capsids as assayed by hemagglutination inhibition titers (HI) and serum neutralization (SN) titers in each species. Subsequent challenge testing of the test animal with virulent parvovirus can be used to correlate immune responses as measures above with protection against disease.

5. Diagnostic Uses of Empty Viral Capsids

Immunogenic empty viral capsids can be used to diagnose viral infection. The capsids can be used to raise a panel of monoclonal antibodies and polyclonal antisera which recognize various epitopes on the virion protein. These monoclonal and/or polyclonals can be used individually or together as capture antibody for immunoassay in the RIA or EIA format, to detect the presence of virus in urine, blood, or feces.

Alternately, the capsids themselves can be used as antigen for an immunoassay to detect the presence of antibody in urine, blood, or feces. Particularly preferred immunoassay are solid phase immunometric assays (enzymetrio radiometric). In such assays, the capsid is immobilized on a solid phase to provide an immunoadsorbent. The immunoadsorbent is then incubated with a sample of bodily fluid to be tested under conditions sufficient for antibody reactive with the capsid to complex with ummobilized capsid. The immunoadsorbent is separated from the sample and anti-capsid antibody associated with the immunoadsorbent is determined as an indication of the antiviral antibody in the sample. Antibody bound to the immunoadsorbent is generally determined by incubating the immunoadsorbent with a labeled (radioisotopically or enzymatically) antibody against antibody of the species from which the sample is derived and detecting label associated with the immunoadsorbent.

The invention is illustrated further by the following examples.

EXAMPLES

Materials & Methods

Restriction Enzyme Digestion:

Enzymes were obtained from New England Biolabs or Boehringer-Mannheim. Digests were performed as described (Maniatis, T., Fritsch, E. F. and Sambrook, J., 1982, Molecular Cloning: A Laboratory Manual. Cold Spring Harbor Laboratory, Cold Spring Harbor, N.Y., pp. 104–105.), with buffer compositions as follows: low salt buffer=10 mM Tris-HCl, pH7.5, 10 mM $MgCl_2$, 1 mM dithiothreitol, 100 ug/ml bovine serum albumin; medium salt buffer=50 mM NaCl, 10 mM Tris-CHl, pH7.5, 10 mM, $MgCl_2$, 1 mM dithiothreitol, 100 ug/ml bovine serum albumin; high salt buffer=100 mM NaCl, 50 mM Tris-HCl, pH7.5, 10 mM $MgCl_2$, 1 mM dithiothreitol, 100 ug/ml bovine serum albumin; SmaI buffer=20 mM KCl, 10 mM Tris-HCl, pH7.5, 10 mM $MgCl_2$, 1 mM dithiothreitol, 100 ug/ml bovine serum albumin. Digests were incubated at 37° C. for 1 hr unless otherwise specified.

Treatment of DNA with Calf Intestinal Phosphatase:

DNA was dephosphorylated in 50 mM Tris-HCl pH9.0, 1.0 mM $MgCl_2$, 0.1 mM $ZnCl_2$ and 1 mM spermidine with 1 ul of calf intestinal phosphatase (Boehringer-Mannheim, 23 units/ul) at 37° C. for 30 min, sometimes followed by a second 30 min incubation with another 1 ul of enzyme.

Treatment of DNA with DNA Polymerase, Large Fragment (Klenow):

Klenow enzyme was obtained from New England Biolabs and used as described (Maniatis, T., Fritsch, E. F. and Sambrook, J., 1982. Molecular Cloning: A Laboratory Manual. Cold Spring Harbor Laboratory, Cold Spring Harbor, N.Y., pp. 112–113).

Gel-Purification of Restriction Fragments:

DNA was fractionated by size on low-melt agarose (ranging from 0.7% to 3%) gels run in 40 mM Tris-acetate pH8.0, 2 mM EDTA. The DNA fragment of interest was excised from gel, liquified at 70° C. and diluted in 200 mM NaCl, 50 mM Tris, pH7.5, 1 mM EDTA. The DNA was extracted with phenol, then phenol:chloroform (1:1) and ethanol precipitated.

Ligation of DNA Fragments:

T4 DNA Ligase was obtained from Boehringer Mannheim. Ligation were performed in 50 mM Tris, pH7.4, 10 mM $mgCl_2$, 10 mM dithiothreitol, 1 mM spermidine, 1 mM adenosine triphosphate, 0.1 mg/ml bovine serum albumin, 1u T4 DNA ligase, at 15° C. for 30 min to 3 days unless otherwise specified.

Phosphorylation of Linkers and Ligation to DNA:

Linkers and T4 polynucleotide kinase were obtained from New England BioLabs. Linkers were phosphorylated and ligated as described (Maniatis, T., Fritsch, E. F. and Sambrook, J., 1982. Molecular Cloning: A Laboratory Manual. Cold Spring Harbor Laboratory, Cold Spring Harbor, N.Y. pp 396–397).

*E.coli* Transformation:

*E.coli* cells were made competent and transformed with DNA as described (Maniatis T., Fritsch, E. F. and Sambrook, J., 1982. Molecular Cloning: A Laboratory Manual. Cold Spring Harbor, N.Y., pp. 250—251).

Isolation and Purification of Plasmid DNA:

Preparation of plasmid DNA and purification by cesium chloride-ethidium bromide gradient centrifugation are performed as described (Maniatis, T., Fritsch, E. F. and Sambrook, J., 1982. Molecular Cloning: A Laboratory Manual. Cold Spring Harbor Laboratory, Cold Spring Harbor, N.Y., pp. 90, 91, 93, 94).

Example 1

Molecular Cloning of CPV RF DNA Sequences

FIG. 1 summarizes the steps involved in the molecular cloning of CPV RF DNA sequences into the prokaryotic vector pEMBL18+ [Dente et al., *Nucleic Acids Res.*, 11, 1645 (1983)]. CPV RF DNA (a gift from Colin Parrish, Cornell University, Ithaca, N.Y.) was cleaved by partial digestion with the restriction nuclease HaeIII. Because there are five HaeIII sites in CPV RF DNA [McMaster et al, *J. Virol.*, 38 368 (1981)], there are fourteen possible products of partial HaeIII digestion; our goal in this experiment was to isolate bacterial clones carrying large partial digestion products, ie. clones carrying most or all of the CPV DNA sequence.

Digested CPV DNA was purified by phenol-chloroform extraction and concentrated by ehtanol precipitation. It was then ligated into the SmaI site of the plasmid vector pEMBL18+ [Dente et al, *Nucleic Acids Res.* 11, 1645 (1983)]. In addition to linearization of the vector with SmaI, the linearized vector DNA was treated with calf intestine phosphate (CIP) to remove the terminal 5' phosphates, a treatment which prevents its recircularization. The ligated DNAs were transformed into the *E. coli* strain JM101 [Messing et al. *Nucleic Acids Res.* 9 309 (1981)] and transformants were spread on lactose MacConkey agar plates [MacConkey, *J. Hyg.* 5: 330 (1905)]. Transformants containing recombinant plasmids were identified by colony hybridization (Grunstein and Hogness, *Proc. Nat'l Acad. Sci., USA* 72, 3961 (1971)); hybridization probes used were the 1.4 kb and 1.1 kb HaeIII fragments of CPV RF DNA, labeled with $^{32}$P by nick translation. Two of the recombinant clones identified, designated pAbT200 and pAbT201, were used for subsequent cloning experiments.

pAbT200 contains approximately 64% of the CPV genome, including the genes encoding VP1 and VP2', together with their endogenous promotor. pAbT201 contains approximately 95% of the CPV genome; it is missing only the extreme 5' terminal sequences of the virus, and contains the entire VP1 and VP2' coding sequences and their endogenous promotor.

Example II

Subcloning CPV DNA Sequences into the DOL Vector

CPV DNA sequences from clone pAbT200 were subcloned into the retroviral vector DOL [B. Roberts, Pers. Comm.] as diagrammed in FIG. 2. DOL DNA (a gift of Dr. B. Roberts, Harvard Medical School) was linearized with BamHI. After digestion, the recessed 3' termini of the digested DNA were filled in using large fragment of DNA polymerase I (Klenow fragment) in the presence of the four deoxynucleotide triphosphates. Lastly, the terminal 5' phosphates were removed from the vector DNA by CIP. CPV DNA was prepared from clone pAbT200 by digestion with TaqI, which cleaves once in the CPV sequence, 24 bases upstream from the VP1 coding sequence, and a number of times in the plasmid vector, including at a site just beyond the inserted CPV DNA, to release a 2.73 kb fragment. This 2.73 kb fragment, which contains the entire VP1-VP2' coding sequence, an additional 24 bases upstream from this sequence, and a few bases derived from the PEMBL18+ vector, was purified by conventional techniques, and the recessed 3' termini of this fragment were repaired using the Klenow fragment of DNA polymerase I. This fragment was ligated to the DOL vector, and ligated DNAs were used to transform *E. coli* strain HB101 [Boyer et al., *J. Mol. Biol.* 41 459 (1969)]. Transformed cells were spread on LB agar plates containing 50 ug/ml of kanamycin. The desired recombinant, designated pAbT210, contained a 2.73 kb CPV DNA fragment inserted at the BamHI site of DOL. This fragment is flanked by BamHI sites regenerated by the ligation of the modified ends of the DOL and CPV DNAS.

Example III

Construction of the Plasmid Vector pdMMTneo$^R$ (pAbT230)

The plasmid vector pdMMTneo$^R$ (pAbT230) was derived from pdBPVMMTneo$^R$ [Law et al. *Mol. Cell Biol.* 3, 2110 (1983)] as outlined in FIG. 3. *E. coli* strain HB101 carrying the plasmid pdBPVMMTneo$^R$ was obtained from the American Type Culture Collection (ATCC #37224). Preparative amounts of this plasmid were prepared by conventional techniques and the DNA was digested with BamHI. This digestion yields two DNA fragments: a 7.95 kb fragment consisting of the entire BPV genome, linearized at the unique BamHI site; and a 6.65 kb fragment consisting of pML2d DNA which carries the pBR322 origin of replication and the B-lactamase gene [Lusky & Botchan, *Nature* 293, 79 1981]; the mouse metallothionein I promoter; the neomycin phosphotransferase gene (neo$^R$) from Tn5; and the small t antigen splicing signals and 3' transcriptional processing signals of SV40. These digestion products were separated from each other and purified using conventional techniques. The BPV fragment was reserved for use in subsequent cloning experiments (see Example IV); the 6.65 kb fragment was self-ligated and used to transform *E. coli* HB101. Transformed bacterial were plated on LB agar containing 40 ug/ml ampicillin. The desired transformant, a plasmid vector designated pAbT230, was prepared and used for subsequent cloning experiments.

Example IV

Construction of Chimeric CPV/BPV Plasmids

The construction of CPV/BPV recombinant plasmids is outlined in FIGS. 4–6. In general, each construction consisted of two steps: (1) the insertion of the appropriate CPV DNA fragment into pAbT230; (2) the insertion of the BPV genome into the pAbT230: CPV recombinant. Three different cloning schemes were employed; these yielded three different CPV/BPV constructs.

A. Construction of CPV/BPV recombinant pAbT241

The first step in the construction of the CPV/BPV recombinant pAbT241 was the insertion of the CPV DNA containing structural genes for the capsid proteins VP1 and VP2' adjacent to the mouse metallothione (MMT) promoter in the vector pAbT230. The construction is designed to permit the MMT promoter to direct expression of the CPV structural genes in the eukaryotic cell. pAbT230 was digested with BglII, which cuts the plasmid once between the MMT promoter and the neo$^R$ gene (see FIG. 4); the terminal 5' phosphates were then removed from the linearized vector DNA with CIP.

DNA encoding the VP1 and VP2' structural genes was isolated from the plasmid pAbT200 by BamHI digestion which liberates a 2.73 kb CPV DNA fragment carrying these genes. This fragment was ligated to the BglII-digested, phosphatase-treated pAbT230 plasmid; this ligation is possible because the enzymes BamHI and BglII yield DNA fragments with identical protruding 5' cohesive termini. The ligated DNAs were transformed into the *E. coli* strain HB101, and transformants were grown on LB agar containing 40 ug/ml of ampicillin.

This ligation yielded two classes of recombinant plasmids which differ by the particular orientation of the CPV DNA with respect to the MMT promotor. In order to distinguish between these two classes of recombinants, as well as to distinguish between recombinant and non-recombinant plasmid DNAs were digested with BamHI and BglII. The products of this double digestion are diagnostic for the orientation of the CPV DNA fragment: in the desired recombinant, in which the 5' end of the CPV structural genes are adjacent to the MMT promoter, the double digest yields fragments of 5.74 and 3.84 kb; in the opposite orientation, the double digest yields fragments of 6.15 and 3.43 kb. Those transformants carrying pAbT230 without inserted CPV DNA gave fragments of 3.84 and 5.74 kb.

The desired recombinant was identified by its BamHI/BglII restriction pattern and designated pAbT240. In the second step of the construction of the CPV/BPV recombinant, the BPV genome was inserted into the unique BamHI site of pAbT240. pAbT240 was digested with BamHI and the ends of the linear digestion product were treated with CIP to remove teminal 5' phosphates. BPV genomic DNA, linearized at the unique BamHI site, was prepared as described in Example III and ligated to the pAbT240 plasmid. The ligated DNAs were transformed into E.coli strain HB101, and transformants were grown on LB agar containing 40 ug/ml of ampicillin.

Plasmid DNA was isolated from transformed cells and analyzed for the presence of BPV sequences by BamHI digestion: recombinants contained, in addition to the 9.58 kb pAbT240 fragment, the 7.93 kb BPV DNA fragment.

Again, this ligation yielded two classes of recombinant plasmids which differed in the orientation of BPV sequences with respect to the CPV DNA sequences. These two classes of recombinants could be distinguished by digestion of the recombinants with EcoRI. Clones in which CPV and BPV transcription units were aligned in the same direction (see FIG. 4) gave EcoRI restriction fragments of 12.5 kb and 5.0 kb. One of these clones, designated pAbT241, was selected for subsequent experiments.

The CPV/BPV recombinant pAbT241 has the following features:

(1) it can be shuttled between prokaryotic and eukaryotic host cells, since it contains both the necessary pBR322-derived sequences as well as the entire BPV genome;

(2) it carries the eukaryotic MMT promoter just upstream from the structural genes of CPV, which permits expression of these genes under the direction of the MMT promoter in eukaryotic cells, (3) it carries the neomycin phosphotransferase gene together with SV40 transcriptional signals just downstream from the CPV structural genes: this gene is also expressed under the direction of the MMT promoter in eukaryotic cells.

B. Construction of CPV/BPV recombinant pAbT243

Figure 5:
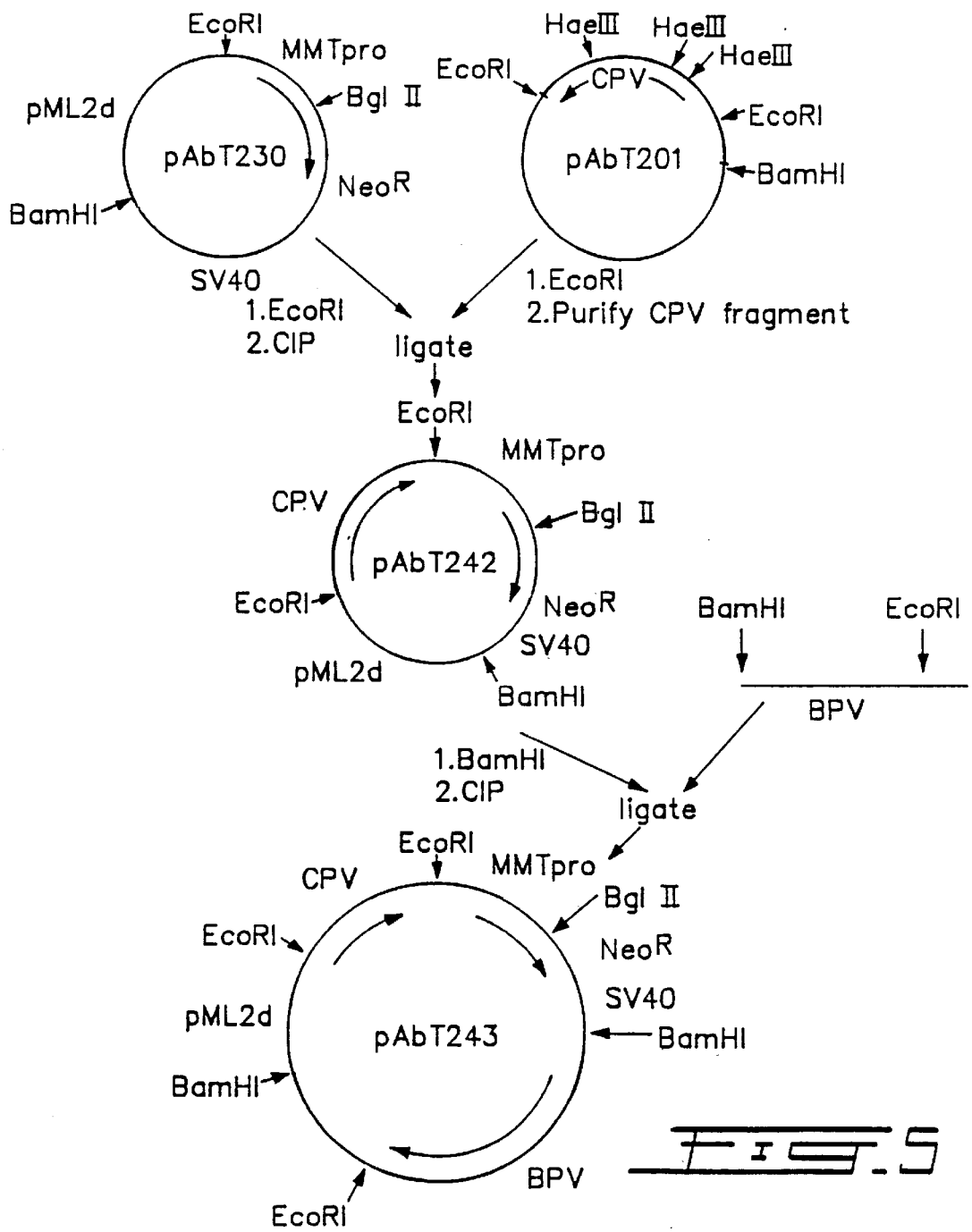
Figure 6:
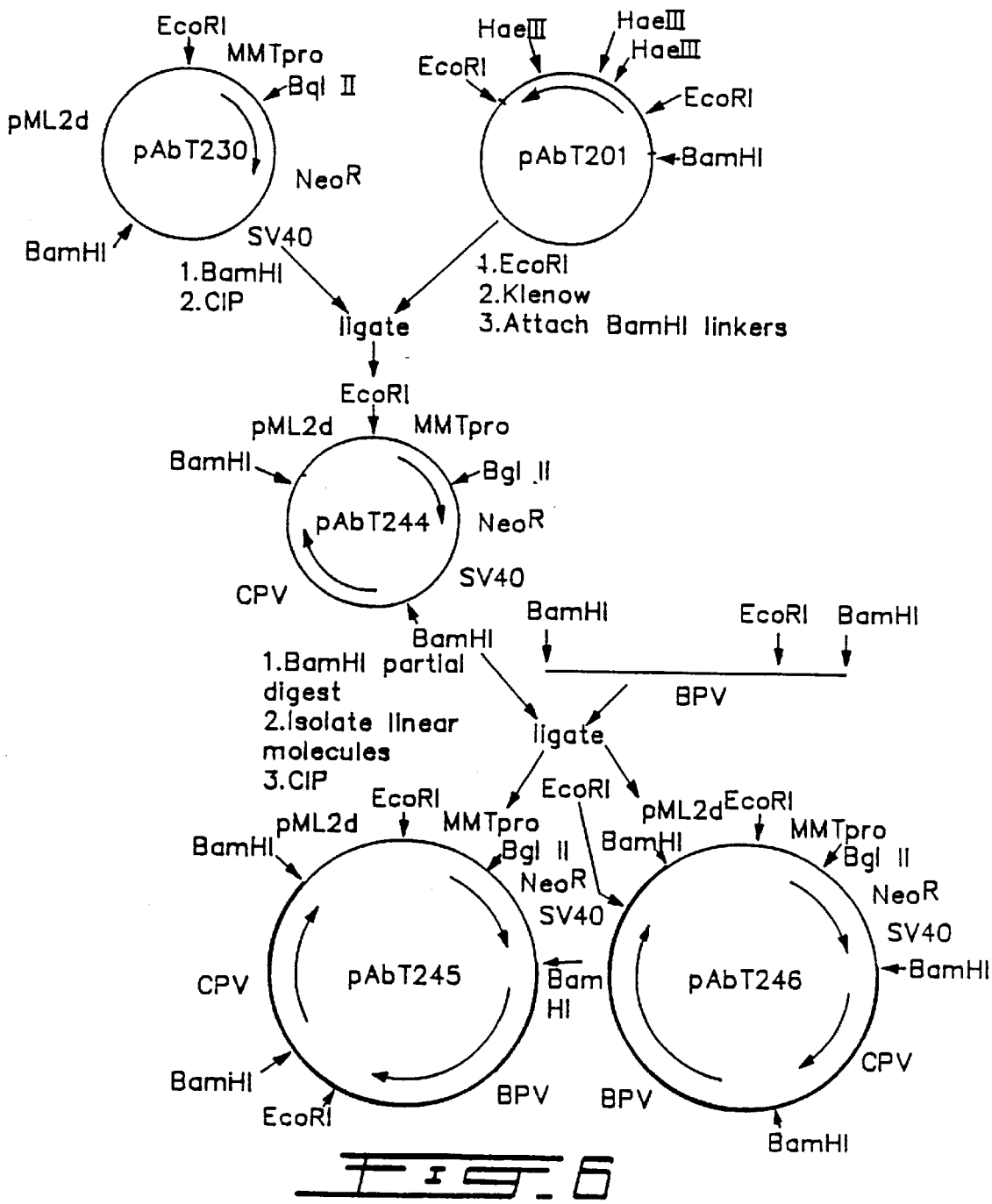

The first step in the construction of the CPV/BPV recombinant pAbT243 was the insertion of the CPV DNA containing structural genes for the capsid proteins VP1 and VP2' together with their promotor into the vector pAbT230.

pAbT230 was digested with EcoRI, which cuts the plasmid once between the pML2 and the MMT promotor sequences (see FIG. 5); the terminal 5' phosphates were then removed from the linearized vector DNA with CIP.

DNA encoding the VP1 and VP2' structural genes and their promotor was isolated from the plasmid pAbT201 by EcoRI digestion which liberates a 4.14 kb CPV DNA fragment carrying these genes. This fragment was ligated to the EcoRI-digested, phosphatse-treated pAbT230 plasmid. The ligated DNAs were transformed into the *E. coli* strain HB101, and transformants were grown on LB agar containing 40 ug/ml of ampicillin.

This ligation yielded two classes of recombinant plasmids, which differ by the particular orientation of the CPV DNA with respect to the vector DNA sequences. In order to distinguish between these two classes of recombinants, as well as to distinguish between recombinant and non-recombinant plasmids, plasmid DNAs were digested with BglII. The products of this digestion are diagnostic for the presence and the orientation of the CPV DNA fragment: BglII digestion of the non-recombinant pAbT230 yields a linear molecule of 9.58 kb; the recombinant in which the CPV and the MMT neo$^R$ transcription units are aligned in the same direction yields two fragments, 7.16 and 3.95 kb; and in the opposite orientation, BglII digestion products are 6.58 and 4.17 kb.

The recombinant in which the CPV and MMTneo$^R$ transcription units are aligned in the same direction was designated pAbT242 and used in the second step of the construction of this CPV-BPV recombinant. In this step, the BPV genome was inserted into the unique BamHI site of pAbT242. pAbT242 was digested with BamHI and the ends of the linear digestion product were treated with CIP to remove terminal 5' phosphates. BPV genomic DNA, linearized at the unique BamHI site, was prepared as described in Example III and ligated to the pAbT242 plasmid. The ligated DNAs were transformed into *E. coli* strain HB101, and the transformants were grown on LB agar containing 40 ug/ml of ampicillin.

Plasmid DNA was isolated from transformed cells and analyzed for the presence of BPV sequences by BamHI digestion: recombinants contained, in addition to the 10.75 kb pAbT242 fragment, the 7.93 kb BPV DNA fragment.

Again, this ligation yielded two classes of recombinant plasmids which differed in the orientation of BPV sequences with respect to the CPV DNA sequences. These two classes of recombinants could be distinguished by digestion of the recombinants with EcoRI and SalI. Clones in which CPV and BPV transcription units were aligned in the same direction (see FIG. 5) gave four restriction fragments when digested with EcoRI and SalI; the sizes of these fragments were 9.9, 3.8, 2.6 and 2.3 kb. One of these clones, designated pAbT243, was selected for subsequent experiments.

The CPV/BPV recombinant pAbT243 has the following features:

1. it can be shuttled between prokaryotic and eukaryotic host cells, since it contains both the necessary pBR322-derived sequences as well as the entire BPV genome;
2. it carries a transcriptional cassette composed of the MMT promotor, the neomycin phosphotransferase gene, and the SV40 early region transcriptional processing signals, which permits antibiotic selection of transformed eukaryotic cells;
3. it carries the CPV genes encoding the capsid proteins VP1 and VP2', together with their associated CPV promotor, which can direct their expression in cell lines transformed by this plasmid.

C. Construction of CPV/BPV recombinant pAbT245

The first step in the construction of the CPV/BPV recombinant pAbT245 was the insertion of the CPV DNA containing structural genes for the capsid proteins VP1 and VP2' together with their promoter into the vector pAbT230. pAbT230 was digested with BamHI which cuts the plasmid once, between the pML2 and the MMT promoter sequences (see FIG. 6); the terminal 5' phosphates were then removed from the linearized vector DNA with CIP.

DNA encoding the VP1 and VP2' structural genes and their promotor was isolated from the plasmid pAbT201 by EcoRI digestion, which liberates a 4.14 kb CPV DNA fragment carrying these genes. The recessed 3' termini of this fragment were filled in using the Klenow fragment of DNA polymerase I in the presence of the four deoxynucleotide triphosphates. Phosphorylated BamHI linkers were then ligated to the ends of this DNA fragment, and the linkered fragment was digested with BamHI and purified.

This modified fragment was ligated to the BamHI-digested, phosphatase-treated pAbT230 plasmid. The ligated DNAs were transformed into the *E. coli* strain HB101, and transformants were grown on LB agar containing 40 ug/ml of ampicillin.

This ligation yielded two classes of recombinant plasmids which differ by the particular orientation of the CPV DNA with respect to vector DNA sequences. In order to distinguish between these two classes of recombinants, as well as to distinguish between recombinant and non-recombinant plasmids, plasmid DNAs digested with BglII. The products of this digestion are diagnostic for the presence and orientation of the CPV DNA fragment. BglII digestion of the non-recombinant pAbT230 yields a linear molecule of 9.58 kb; the recombinant in which the CPV and the MMTneo$^R$ trnascription units are aligned in the same direction yields two fragments, 6.24 and 4.51 kb; and in the opposite orientation, BglII digestion products are 6.82 and 3.93 kb.

The recombinant in which the CPV and the MMTneo$^R$ transcription units are aligned in the same direction was designated pAbT244 and used in the next step of the construction of this CPV-BPV recombinant. In this step, the BPV genome was inserted into one of the two BamHI sites of pAbT244. pAbT244 was partially digested with BamHI, and the resultant linear molecules were treated with CIP, then purified on neutral agarose gels.

BPV genomic DNA, linearized at the unique BamHI site, was prepared as described in Example III and ligated to the pAbT240 plasmid. The ligated DNAs were transformed into *E. coli* strain HB101, and transformants were grown on LB agar containing 40 ug/ml of ampicillin.

Plasmid DNA was isolated from transformed cells and analyzed for:

1. the presence of BPV DNA sequence;
2. the BamHI site into which BPV DNA was inserted;
3. the orientation of the BPV sequences with respect to CPV sequences.

This analysis was performed by digestion of plasmid DNAs with EcoRI, which gave a unique restriction pattern for each of the four possible sequence orientations of CPV and BPV. Two clones, pAbT245 and pAbT246, carried the CPV and BPV transcription units aligned in the same direction, but differ in the site of insertion of BPV DNA. Clone pAbT245 was chosen for further analysis.

Like the CPV/BPV recombinant pAbT243 described above, pAbT245 can be shuttled between prokaryotic and eukaryotic host cells, and transformed eukaryotic host cells can be selected by virtue of their antibiotic resistance. Finally, pAbT245 also carries the genes encoding the CPV capsid proteins VP1 and VP2' together with their associated CPV promoter, which can direct their expression in eukaryotic cells transformed by this plasmid.

Example V

Generation of Cell Lines Expressing Canine Parvovirus VP1 and VP2'

A. Cells and Media

NIH 3T3 cells were received from Bryan Roberts (Harvard Medical School, Boston Mass.). Cells were maintained in DME 10% calf serum (CS) and sodium pyruvate (Gibco, No. 430-2100). A-72 canine tumor cells (ATCC No. CRL 1542) were maintained in a 1:1 mixture of L-15 (Leibovitz media, Gibco, No. 430-1300) and McCoys 5A media modified (Gibco, No. 430-1500) containing 10% fetal calf serum (FCS). Calf serum and fetal bovine serum were purchased from HyClone Laboratories, Inc.; geneticin (G418) was purchased from Gibco. Each G418 lot was titered for cytotoxicity on both NIH 3T3 cells and A72 cells.

B. Transfection of Cells with Chimeric CPV/BPV Plasmids pAbT241, pAbT243, and pAbT245.

All of the chimeric CPV/BPV plasmids have several features in common as described in Example IV: the presence of the BPV genome and the neo$^R$ gene in the plasmids provide two mechanisms by which to select cells which have taken up the plamids after transfection. A wide variety of eukaryotic cells grown in culture can be made to take up exogenously added DNA using standard transfection procedures (Cepko et al., *Cell* 37, 1053 (1984)).

1. Transfection of NIH 3T3 Cells with pAbT241 (Transformation No. VII) and pAbT243 (Transformation No. VIII):

NIH 3T3 cells were seeded at $5 \times 10^5$ cells/10 cm plate one day prior to transfection. Cells were fed approximately four hours prior to transfection at which time they were approximately 40% confluent. Cells were transfected with 10 ug of each plasmid as a calcium-phosphate precipitate. Specifically, 10 ug of pAbT241 (29 ul stock) or pAbT243 (8.68 ul stock) was mixed with 421 ul or 442 ul respectively of HEPES buffer I (137 mM NaCl, 5 mM KCl, 0.7 mM $Na_2HPO_4$ 6 mM Dextrose, 21 mM HEPES, pH7.1). 32 ul of 2 M $CaCl_2$ was added slowly while mixing.

The precipitates were allowed to sit at RT for 40 min, at which time the precipitates were added to the NIH 3T3 cells in 2.0 ml of DME+10% CS. After 20 min at 37° C. in a $CO_2$ incubator, an additional 3.0 ml of DME+10% CS was added. At four hours after the addition of DNA the cells were washed 2× with DME and glycerol shocked by incubating with 3.0 ml of 15% glycerol in 0.3 M HEPES buffered saline for 3.5 min at RT. After the shock, they were washed 4× with DME and then incubated in 5.0 ml of DME+10% CS at 38° C. 18 hours later, the cells were split 1:5 per 10 cm. plate in DME+10% CS. 48 hours later, the cells were washed and incubated in DME+10% CS containing 800 ug/ml of G418. Media containing G418 was changed every three days.

Single G418$^R$ colonies were picked at 18 days after transfection using sterile cloning rings and grown to confluency in 24 well multiplates (Falcon) in DME+10% CS. Resistant cells were then transferred to 3.5 cm plates for amplification and finally to two 10 cm plates. One 10 cm plate of each isolated foci was frozen in two ampoules (freezing media: DME+20% FCS; 12.5% dimethylsulfoxide (DMSO)) and stored in liquid nitrogen. The second plate of each foci was used as a stock plate.

Each transfection yielded multiple G418 resistant foci. Several foci were assayed for CPV-specific RNA transcripts by means of a RNA dot blot assay using a radiolabelled CPV DNA as a hybridization probe using standard protocols (see Example VI). Individual foci which were determined to produce CPV-specific transcripts were chosen for further analysis.

2. Transfection of NIH 3T3 Cells with pAbT245 (Transformation No. X).

NIH 3T3 cells were seeded at $2.5 \times 10^5$ per 6 cm plate two days prior to transfection. Cells were re-fed four hours prior to transfection, at which time they were approximately 80% confluent. The cells were transfected with 5 ug of pAbT245 as a calcium-phosphate precipitate. Specifically, 5 ug DNA (6.4 ul stock) was mixed with 10 ug (2 ul stock) of calf thymus carrier DNA (Boehringer-Mannheim) in 442 ul HEPES buffer I, followed by the addition of 50 ul of 1.25 M CaCl solution while slowly vortexing. The precipitate was allowed to sit at RT for 30 min. The entire DNA precipitate was then added to the cells drop-wise in 5.0 ml of DME+ 10% CS, the plates were gently rocked and then incubated at 37° C. for 4 hr. At the end of the incubation period, the media was aspirated off and 0.7 ml of DME+10% CS containing 20% DMSO was added to shock the cells. The cells were incubated at RT for 1 min, then washed twice with phosphate buffered saline (PBS). Then 5.0 ml of DME+10% CS was added and the cells incubated for 14 hr at 37° C. The transfected cells were then split 1:3 into 6 cm plates. After two days, the cells were re-fed with DME+10% CS containing G418 at 800 ug/ml. Media and fresh G418 was added every third day. After 14–21 days well-isolated foci were picked and amplified as described above, except that cells were maintained in the presence of G418 (200 ug/ml).

3. Transfection of A-72 Cells with pAbT245
   (Transformation No. XII) and pAbT241
   (Transformation No. XIII).

Transfections were performed as described by Shih et al., [*Proc. Nat'l Acad. USA* 76, 5714 (1979)]. Specifically, A-72 cells were seeded at $5\times10^5$ cells per 10 cm plate one day prior to transfection. Four hours before transfection they were re-fed with fresh media (L-15+McCoys 1:1, 10%FSC). Each plate was transfected with 10 ug of plasmid DNA as follows. 10 ug of plasmid was mixed with 30 ug of salmon sperm DNA (Sigma) and water added to 440 ul, followed by the addition of 60 ul of 2 M $CaCl_2$. This was added drop-wise to a solution of 440 of 2× HEPES buffered saline (HEPES 10 g/l, NaCl 16 g/l pH7.10) mixed with 10 ul of 100× phosphate buffer (70 mM $NaPO_4$ 70 mM $NaH_2PO_4$) with air bubbling through the solution. The DNA was allowed to incubate for 30 min at RT and then the entire 1.0 ml was added to the A-72 cells in 10 ml of media. The cells were gently rocked and incubated at 37° C. in a $CO_2$ incubator for 4–6 hours. The cells were then fed with fresh media. After three days the transfected cells were split 1:4 into fresh media containing G418 at 1200 ug per ml. Fresh media plus G418 was added every three days. After 14–18 days single-well isolated foci were picked with a pasteur pipet after a gentle treatment of the entire plate with 0.056% trypsin for one minute. Isolated foci were amplified and stored as described above, but were kept in G418 (200 ug/ml).

Example VI

RNA Dot Blot Assay for CPV-Specific RNA

Two different protocols were used for the RNA dot blot assays. In the first method, individual foci from transformation #VII (4 foci), #VIII (17 foci), and #X (12 foci) were grown in 24 well multiplates (Falcon) to confluency as described in Example 5. Cells were washed 2× in PBS, then lysed for 30 min at 37° C. with 200 ul of a 1:1 solution of GTC (4 M guanidium thiocyanate, 25 mM Na-citrate, pH7, 0.5% lauryl sarkosine) and DMSO. 90 ul of lysate was filtered through nitrocellulose pre-wet in 20× SSC (3 M NaCl, 0.3 M Na-citrate, pH7.0) in an S&S minifold apparatus. The samples were washed 2× with 20× SSC. Following hybridization under standard conditions with $^{32}$P-labeled CPV DNA, the filter was autoradiographed. The results are presented in Table 1.

TABLE 1

Expression of CPV Structural Genes in 3T3 Cells Transformed with pAbT241 (Transformation #VII), pAbT243 (Transformation #VIII) and pAbT245 (Transformation #X):

| Transformation Number | Total Foci Screened | Total Foci Expressing CPV RNA |
|---|---|---|
| VII | 4 | 1 |
| VIII | 17 | 6 |
| X | 12 | 9 |

Individual foci from transformation #XII (15 foci) and #XIII (11 foci) were screened for CPV-hybridizing RNA in the following manner: cells were grown to confluency in 5 cm plates as described above. Cells were washed in PBS, then scraped into 1 ml of PBS and harvested by centrifugation, washed 1× in 1 ml of PBS, then resuspended in 45 ul of 10 mM Tris Cl (pH8), 1 mM EDTA. 5 ul of 5% NP40 was added to each sample, and samples were incubated on ice for 5 min. An additional 5 ul of NP40 was then added, and incubation on ice was continued for an additional 5 min, after which time nuclei were pelleted by centrifugation for 2.5 min in the microfuge. 50 ul of the supernatant was then added to a mixture of 30 ul of 20× SSC and 20 ul of 37% (w/v) of formaldehyde. The mixtures were incubated for 15 minutes at 60° C., and samples were spotted onto nitrocellulose and processed as described in the preceding paragraph. All of the 14 foci from transformation #XII contained some level of CPV-hybridizing DNA; 6 of the 11 foci from transformation #13 also exhibited CPV-specific RNA (Table 2).

TABLE 2

Expression of CPV Structural Genes in A-72 Cells Transformed with pAbT245 (Transformation #XII) and pAbT243 (Transformation #XIII):

| Transformation Number | Focus Number | RNA Dot Blot | HA Units In Pellet |
|---|---|---|---|
| XII | 1 | + | 320 |
| | 2 | +++ | 1280 |
| | 3 | + | 160 |
| | 4 | + | 160 |
| | 5 | +++ | N.D. |
| | 6 | +/− | 80 |
| | 7 | +++ | N.D. |
| | 9 | + | 320 |
| | 10 | + | 160 |
| | 11 | +++ | 80 |
| | 12 | +/− | 80 |
| | 13 | +++ | 640 |
| | 14 | + | 80 |
| | 15 | + | 10,240 |
| XIII | 1 | − | 320 |
| | 2 | − | N.D. |
| | 3 | +/− | 160 |
| | 4 | − | 320 |
| | 5 | + | 5120 |
| | 6 | + | 1280 |
| | 7 | +/− | 80 |
| | 9 | + | 1280 |
| | 10 | − | 160 |
| | 12 | − | 0 |
| | 14 | +/− | 640 |

N.D.: not determined

Certain individual transformants which displayed CPV-hybridizing RNA in these experiments were chosen for further analysis. There were designated transformant VII-1, VIII-1, X-1, X-2, and X-5. In addition, all foci from transformants XII and XIII were assayed for the production of assembled parvovirus capsids by the hemagglutination assay as described in Example X below (Table 2).

Example VII

Preparation of CPV Capsids

The preparation of hemagglutination activity (i.e., intact capsids) from CPV-infected A-72 cells was typically performed in the following manner. All operations were carried out at 4° C. or on ice, unless otherwise reported. Approximately 300 to 1000 ml of culture medium from infected cells was concentrated by ultrafiltration (Amicon stirred cell, YM10 membrane) and then clarified of cell debris by centrifugation at 14,500 g (10,000 rpm, Sorvall SA600 rotor) for 15 min. The sample (supernatant) was spun at 58,000 g (25,000 rpm Beckman SW50.1 rotor) for 4 hr, after which the resulting virus pellet was resuspended with 1 ml of 50 mM Tris, pH8.0/0.5 mM EDTA. More cellular debris was removed by a chloroform extraction, in which the sample was mixed with 1 ml of chloroform and then spun at 14,500 g (10,000 rpm, Sorvall SA600 rotor). The aqueous phase was then layered onto a linear sucrose gradient, 10 to 40% w/w, and spun for 5.5 hr at 83,000 g (25,000 rpm, Beckman SW28 rotor). The virus band was collected, dialyzed against 50 mM Tris, pH8.0/0.5 mM EDTA buffer to remove the sucrose, and then prepared with CsCl to a density of 1.38 g/ml and spun in the ultracentrifuge at 99,000 g (38,000 rpm, Beckman 70.1 Ti rotor) for 36 hr. Fractions were collected from the density gradient and were assayed for hemmagglutination activity as described in Example X below. The refractive index of each fraction was measured to determine its solution density. Purified CPV was also analyzed by SDS-PAGE as described in Example IX below.

The preparation of hemmagglutination activity from CPV/BPV-transformed cells followed a modification of the same procedure outlined above for virus-infected cells. A pellet prepared from $1.4\times10^8$ transformed cells was suspended with 1 ml of 50 mM Tris, pH8.0/0.5 mM EDTA and lysed by sonication. The sample was submitted to a low-spin centrifugation at 14,500 g, followed by a centrifugation at 58,000 g, and then extracted with chloroform as previously described. The sucrose gradient was omitted, and the sample in Tris/EDTA buffer was applied directly to the CsCl density gradient.

Example VIII

Production of Conventional Antisera

Rabbit polyclonal antisera against CPV were raised using inactivated, purified CPV as antigen. Cesium chloride banded virus was irradiated at 254 nm (UV source lamp Model UV GL-25 mineralight; 1.5 cm from sample) for 3 min at 37° C. The resulting sample was determined to be free of infectious virus by submitting to testing in tissue culture. Approximately 100 ug of protein from the sample was inoculated into female New Zealand white rabbits by a mixture of intradermal and intramuscular injections with complete Freund's adjuvant. Immunizing boosts consisting of 100 to 150 ug protein were given at 1-month intervals by subcutaneous injection, once with incomplete Freund's adjuvant and subsequently without adjuvant. Bleeds were taken from the animals at 7 to 10 days after injection. Serum was heated at 56° C. for 30 min to inactive complement, spun at 12,000 g for 10 min to remove clot, and stored at −20° C.

Mouse monoclonal antibodies against epitopes of CPV were generously given by Dr Colin Parrish and are described in Parrish et al., *Archives of Virol.,* 72 267 (1982).

Example IX

Analysis by Immunoprecipitation of CPV Proteins Produced in Transformed Cells

1) Metabolic Labeling:

CPV/BPV-transformed 3T3 cells were labeled for 24 h in 7.5 ml of media consisting of DME (methionine-free), 10% calf serum, carrier methionine (0.3 mg/100 ml), 2.0 mM glutamine, and 100 uCi of [$^{35}$S]methionine (New England Nuclear). The cells were washed twice with PBS and scraped into 1 ml of immunoprecipitation buffer (IPB), consisting of 10 mM Tris-HCl, pH7.2, 650 mM NaCl, 1% Triton X-100, 1% sodium deoxycholate, 0.1% SDS, 5 mM EDTA, 1 mM phenylmethylsulfonylfluoride, 0.1 mg/ml trypsin inhibitor, and 1 mM ATP. The lysates were stored at 80° C.

2) Preparation of *Staphylococcus Aureus:*

Killed and formalin-fixed *S. aureus* (IgSorb) was obtained as a 10%(w/v) suspension from the Enzyme Center (Malden, Mass.). The cells were washed twice with IPB and pelleted by spinning 5 min in a microfuge (Eppendorf). The cells were resuspended to a final concentration of 10% or 20% (w/v) in IPB.

Preformed complexes of *S. aureus* and IgG were prepared by incubating 5 volumes of 10% (w/v) *S. aureus* with 1 volume of normal serum, 10 min. 0° C. The complexes were pelleted, washed twice, and resuspended to a final concentration of 20% (w/v) in IPB.

3) Immunoprecipitation:

Immunoprecipitations were carried out on cell samples each containing 5 uCi in 0.3 ml of IPB. All incubations with antibodies of *S. aureus* were done with rocking at 4° C. Each sample was precleared by incubating with 50 ul of preformed immune complex (*S aureus*-IgG, 20% [w/v]) for 1 hr and then clarifying by centrifugation in the microfuge, 5 min. The supernatant was transferred to a new test tube and the preclearing was repeated. The resulting supernatant was then treated for another 30 min with 50 ul of 20% (w/v) *S. aureus.* Finally, the supernatant was transferred to a new test tube and incubated overnight with primary antibodies at an appropriate dilution. The next day 50 ul of 10% (w/v) *S. aureus* were added to the sample, and the incubation was continued 30 min. The *S. aureus* complexes were pelleted by centrifugation and washed with 200 ul of IPB. The suspension was layered over a differential sucrose gradient [400 ul of 10% (w/v) sucrose/0.5M NaCl/IPB], and spun for 10 min in a microfuge. The resulting precipitate was washed with 200 ul of IPB and resuspended with 20 ul of gel sample buffer. The sample was heated for 5 min at 100° C., centrifuged to remove the precipitate, and syringed out for application on an SDS gel.

4) SDS-PAGE Gel and Autoradiography:

SDS-polyacrylamide gel electrophoresis (SDS-PAGE) was run on 0.75 mm slab gels under reducing conditions (Laemmli, *Nature* 227, 680 (1970)). The separation gel was 8% acrylamide and contained 375 mM Tris, pH8.8, 0.1% SDS, 0.33% TEMED, and 0.02% ammonium persulfate; the stacking gel was 3% acrylamide and contained 125 mM Tris, pH6.8, 0.1% SDS, 0.1% TEMED, and 0.1% ammonium persulfate. Samples were mixed with equal volumes of 2× sample buffer (125 mM Tris, pH6.8, 4% SDS, 20% glycerol, 10% [v/v] B-mercaptoethanol, and a trace of bromophenol blue) heated for 5 min at 100° C., clarified by a brief centrifugation, and applied to the gel. Electrophoresis was carried out in 25 mM Tris, pH8.3, 192 mM glycine, 0.1% SDS, at about 30 mA until the tracking dye was off the gel. The relative migration of proteins on the gel was compared to a set of $^{14}C$ radioactive molecular weight standards (BRL). Gels were fixed in 30% methanol/10% acetic acid/ 60% $H_2O$, and prepared for autoradiography by a 1 hour incubation in En³Hance (New England Nuclear) followed by a 1 hour incubation in water. Gels were dried in vacuo at 60° C. and then exposed to Kodak X-omat AR-5 film at −80° C.

5) Results:

CPV/BPV-transformed VII-1, VIII-1, X-1, X-2, and X-5 were inspected for expression of VP2' and VP1 by immunoprecipitaion analyses of their [$^{35}S$]methionine-labeled proteins. Tests were initially run on both the culture supernatants and the cell lysates derived from the clones; however, analysis of culture supernatants was discontinued because their low protein concentrations did not provide for definitive signals. The targeted proteins were easily immunoprecipitated from cell lysates, and so positive identification of clones expressing CPV proteins was made from that source. By immunoprecipitation analysis, all five transformants clearly showed production of CPV proteins VP2' and VP1. The successful immunoreactions were reproduced with both our rabbit and mouse −CPV antiserum (1:100 dilution) and with several mouse −CPV monoclonal antibodies (1:1000 dilution; gift of Dr. Colin Parrish), using S. aureus as the precipitating reagent. Similarly, we were able to immunoprecipitate the CPV proteins from clones generated in A-72 cells. Of nine clones tested, five showed very strong positive signals (two were from transformation XII; three were from transformation XIII).

Example X

Hemagglutination (HA) Testing

A hemagglutination assay was used to verify the presence of CPV capsids in samples (Parrish et al., Arch. Virol. 72, 267).

The assay buffer, barbital-buffered saline (BBS), consisted of 32 nM sodium barbital, 28.6 mM sodium acetate, 2.5 mM $MgCl_2$-6 $H_2O$, 0.75 mM $CaCl_2$-2 $H_2O$, 116.8 mM NaCl, and 0.1% bovine serum albumin, adjusted to pH6.2 with 1N HCl. Cell pellets obtained from transformant cells at 100% confluence were suspended in 250 ul of BBS and lysed by sonication (multiple bursts, 50% duty cycle, Sonicator Ultrasonic Processor Model W-225 [Heat Systems Ultrasonics, Inc]). A 25 ul portion of each test sample was mixed with 25 ul of BBS in the first well of a V-well microtiter plate and then serially diluted across using two-fold dilutions. Then 50 ul of a 0.5% solution of rhesus monkey erythrocytes (washed twice in BBS) was added to each cell and the incubation was carried out at 4° C. for 2–16 hours. The HA titer is read as the reverse of the last dilution that gives complete hemagglutination.

Hemagglutination assays were performed on selected CPV/BPV transformants to determine whether those clones were producing assembled parvovirus capsids. All five of the clones tested (VII-1, VIII-1, X-1, X-2, and X-5) showed strong hemagglutination titers (Table 3). The strongest positive clone (X-5) was chosen for further characterization. The yield of HA units from this clone indicated that between $10^7$ and $10^8$ capsid particles per cell were produced (One HA unit is correlated with $2 \times 10^{10}$ capsid particles on the basis of Lowry protein determinations and an empty capsid molecular weight of $4 \times 10^6$ daltons). By comparison, a culture of CPV-infected A-72 cells typically yields $10^9$ particles per cell. Hemagglutination titers were also obtained from BPV/CPV transformed A-72 cells. (See table 2).

TABLE 3

Expression of hemagglutination titers from CPV/BPV transformed 3T3 cells.

| CPV/BPV Transformant Lysate | Total HA Units | |
|---|---|---|
| | In Culture Supernantant | In Cell |
| VII | 0 | 2560 |
| VIII-1 | 0 | 5120 |
| X-1 | 0 | 1280 |
| X-2 | 0 | 2560 |
| X-5 | 0 | 41000 |

Transformed cells were seeded in 10 cm plates at a density of approximately $2 \times 10^5$ cells. Three days after they reached confluency, the cells were harvested and lysed by sonication. HA assay was performed as described in Example X.

Example XI

Characterization of CPV Capsids from X-5 by CsCl Gradient Centrifugation

The hemagglutinating activity of X-5 was detected only in the cell lysate fraction and not in the media supernatant. We carried out a purification of the HA activity to ascertain whether it would behave as empty capsid particles of parvovirus. A lysate was prepared from $1.35\times10^8$ cells of the transformed line. Cellular debris was removed by centrifugation at 14,500 g, and the resulting supernatant was subjected to a high-speed spin at 58,000 g yielding a pellet. The pellet was purified further by choloroform extraction. The sample was resuspended with 1 ml of buffer (50 mM Tris, pH8.0/0.5 mM EDTA) mixed with 1 ml of chloroform, and centrifuged at 14,500 g. This step resulted in extraction of debris into the interphase. The buffer phase was applied to a CsCl gradient (1.38 g/ml) and centrifuged for 36 hours at 99,000 g, 4° C. Fractions were then collected from the bottom of the gradient sample and were assayed for HA units. The HA activity migrated as a peak centered at a density of 1.33 g/ml (refractive index=1.366), which is consistent with the value reported for empty capsids (Bachmann et al, *Intervirology II,* 248 (1979)). This active fraction was shown by SDS gel analysis to be heterogeneous, containing many other protein bands in addition to VP1 and VP2'.

The HA activity of crude cell lysates of X-5 is stable when they are stored frozen at −80° C., and furthermore is unaffected by lyophylization or by freeze-thawing. At 4° C., however, aggregation of capsid particles slowly takes place, which results in substantial loss of HA activity over a few days. The rate of aggregation is subject to buffer and dilution effects. The lost activity can be partially regenerated by sonication. By comparison, crude cell lysates of CPV-infected A-72 cells are stable at 4° C. with respect to their hemagglutination activity. Further investigation of the stability of X-5 capsid particles revealed that the instability was apparently promoted by components of the lysate itself. Samples which are purified further on a sucrose gradient (10–30% w/v) remained fully active even after storage at 4° C. for 3 months.

Although we could not detect any hemagglutinating activity in culture supernatants of X-5, an analysis by SDS-PAGE of several extracellular fractions showed that these nevertheless contained the CPV polypeptides VP2' and VP1 (at approximately 4:1). In these extracellular fractions, as well as in the intracellular cell lysate fraction, the ratio of VP2' to VP1 is identical to the ratio of these proteins in purified CPV.

Example XII

Immunization of Dogs with Empty CPV Capsids Prepared From X-5

A cell lysate was prepared from ten 15 cm plates of confluent X-5 cells by suspending the harvested cell pellet in 1 ml of PBS, freeze-thawing the cell suspension three times and sonicating. The HA titer in the cell lysate was approximately $2 \times 10^5$ HA units/ml. Hemagglutination units were determined as described in Example X.

On day 1, two puppies (from sero-negative bitches) were placed in isolation, serum samples were collected, and each dog was inoculated intramuscularly with 0.3 ml ($6 \times 10^4$ HA units) of cell lysate either in PBS (Dog #215) or with 10% aluminum hydroxide (Dog #214). An additional sero-negative dog was added as a contact control on day 19 (Dog #184). On day 41, the two previously vaccinated dogs were reimmunized as before. All dogs were challenged on day 83 by oronasal inoculation with approximately $2 \times 10^6$ plaque-forming units (PFU) of a virulent post-1980 strain of canine parvovirus (CPV-15, C. Parrish, James A. Baker Institute for Animal Health, Cornell). This strain is antigenically different from the virus from which the structural protein genes were cloned. The post-1980 strain of challenge virus was chosen for three reasons: (i) it is more virulent than the pre-1980 strains and therefore can be monitored more easily, (ii) it is the virus commonly infecting dogs in nature at the present time and (iii) it permitted determination of the efficacy of the vaccine in protection against the post-1980 strains of canine parvovirus.

Dogs were bled at various intervals during the course of the experiment, and serum samples were assayed for hemmagglutination inhibition (HI) titers as described by Parrish et al [*Archives of Virol.* 72, 267 (1982)]. Titers are expressed as the reciprocal of the highest dilution that completely inhibited viral hemmagglutination of rhesus monkey red blood cells, and are a measure of the levels of anti-CPV antibodies in the serum. These results are presented in Table 4, and clearly show an antibody response to the X-5 antigen after vaccination, as well as high levels of anti-CPV antibodies after challenge with the virus. These sera were also tested for the presence of neutralizing anti-CPV antibodies in a PFU reduction assay. Serum neutralization titers (SNT) were determined as follows: sera were heat-inactivated at 56° C. for 30 minutes, then serially diluted. Equal volumes of sera and virus (approximately 40 PFU of CPV strain CPV-95; C. Parrish, James A. Baker Institute for Animal Health) were mixed and incubated at room temperature for one hour, at which time each mixture was added to a monolayer of A-72 cells (P165-178; James A Baker Institute for Animal Health). Plates were incubated for 1 hour at 37° C. with shaking, then overlaid with growth medium containing 0.9% agarose. After 5 days, plates were fixed and stained, and plaques were counted. In control experiments, the virus was titered in the absence of serum; for comparison, virus was also incubated with a control (hyperimmune) serum. These results are presented in Table 4, and show an increase in the SNT of the vaccinated dogs over pre-immune levels, as well as a substantial rise in the SNT of dog 214 as compared to the control dog #184 one day after challenge (the SNT of dog #215 at this time was not determined).

TABLE 4

Pre and Post Challenge Serum Hemagglutination and Serum Neutralization Titers:

| DAY | DOG # | HI | SN TITERS SERUM DILUTION | | | | | |
|---|---|---|---|---|---|---|---|---|
| | | | 5 | 25 | 125 | 625 | 3125 | 15625 |
| 0 | 214 | <10 | 44 | 28 | 30 | — | | |
| | 215 | <10 | 37 | 31 | 32 | — | | |
| 13 | 214 | 80 | 0 | 0 | 1 | — | | |
| | 215 | 40 | 0 | 0 | 8 | — | | |
| 27 | 184 | <10 | 33 | 32 | 30 | — | | |
| | 214 | 40 | 0 | 0 | 15 | — | | |
| | 215 | 20 | 0 | 4 | 18 | — | | |
| 40 (Boost) | 184 | <10 | 24 | 27 | 34 | — | | |
| | 214 | <10 | 0 | 5 | 27 | — | | |
| | 215 | <10 | 0 | 8 | 27 | — | | |
| 76 | 184 | <10 | | | | | | |
| | 214 | 80 | | | | | | |
| | 215 | 40 | | | | | | |
| 83 | 184 | | 36 | 37 | 33 | — | — | — |
| | 214 | | 0 | 0 | 0 | 2 | 27 | 37 |
| | 215 | | — | — | — | — | — | — |
| 92 (10 days post challenge) | 184 | 5120 | | | | | | |
| | 214 | >20480 | | | | | | |
| | 215 | >20480 | | | | | | |

(SNT Titration, diluted 1:100 prior to assay)

| Control Serum (Hyperimmune) | 10240 | 0 | 0 | 0 | 4 | 9 | 27 |

Control titration of the virus, with no serum, gave a titers of 37/42/44 PFU.

In additional studies, the presence of CPV in the serum and feces of dogs challenged with the virus were examined (Table 5). As measured by plaque assay, essentially no PFU were detected in the plasma of vaccinated animals up to four days post-challenge, while a significant level of virus was found in the serum of the control animal three days post-challenge. In addition, the control dog shed much higher viral HA titers in the feces than either vaccinated dog.

TABLE 5

Fecal Hemagglutination Titers and Serum Viral Titers:

| | Dog Number | | | | | |
|---|---|---|---|---|---|---|
| Day After | 184 | | 214 | | 215 | |
| Challenge | HA | PFU | HA | PFU | HA | PFU |
| 2 | 8–16 | 3 | 2 | 0 | 2 | 0 |
| 3 | 2 | $6 \times 10^1$ | 2 | 0 | 2 | 1 |
| 4 | 32–64 | 0 | 8 | 0 | 2–4 | 0 |
| 5 | 1024 | | 4 | | 8–16 | |
| 6 | No. Sample* | | 2–4 | | 2 | |
| 7 | 256–512** | | 2 | | 2 | |

*Dog did not eat - no feces to collect.
**Diarrhea dog #184 this day. All other samples normal.

In addition, the control dog developed diarrhea while the vaccinated animals did not. Clearly the vaccinated dogs were protected against disease; however, there was a limited level of virus replication in the vaccinated dogs as shown by the higher post-challenge serum HI titers and some viral particles shed in the feces. This immune response is comparable to that seen after vaccination of animals with commercially available killed-CPV vaccine.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A plasmid comprising:

a) an origin of replication for a prokaryotic host;

b) an origin of replication for a eukaryotic host;

c) a eukaryotic promoter; and d) a DNA segment that consists essentially of genes encoding parvovirus VP1 and VP2' capsid proteins in self-assembling form, the genes being under the direction of the eukaryotic promoter;

wherein said plasmid is capable of replication in a prokaryotic and a eukaryotic host and capable of expressing empty viral parvoviral capsids in a eukaryotic host.

2. A plasmid of claim 1, wherein the origin of replication is isolated from the plasmid pBR 322, the eukaryotic promoter is the murine metallothionein promoter, and the gene which provides a selectable phenotypic trait for eukaryotic host is the $Neo^R$ gene.

3. A plasmid of claim 1, wherein the $Neo^R$ gene is located adjacent and 3' to the VP1 and VP2' structural genes so that the gene is under the direction of the murine metallothionein promoter.

4. A plasmid of claim 1, further comprising genes isolated from bovine papilloma virus which provide for episomal replication of the vector in a eukaryotic host.

5. A plasmid of claim 1, wherein the eukaryotic promoter is the endogenous parvovirus promoter for the genes encoding VP1 and VP2' proteins.

6. The chimeric plasmids pAbT241, pAbT243, pAbT245, and functional equivalents thereof.

7. A transfected eukaryotic cell capable of stably producing self-assembled, immunogenic, parvovirus empty capsids.

8. A transfected eukaryotic cell of claim 7, wherein the parvoviral capsids are canine parvoviral capsids.

9. A transfected eukaryotic cell of claim 8, which is a murine 3T3 cell, a murine C127 cell or a canine A72 cell.

10. An eukaryotic cell transfected with a plasmid selected from the group consisting of pAbT241, pAbT243 and pAbT245.

11. A eukaryotic cell of claim 10, which is a murine 3T3 cell, a murine C127 cell or a canine A72 cell.

12. A DNA expression vector which contains a sufficient portion of a parvovirus genome to encode parvovirus VP1 and VP2' capsid proteins, but excluding the extreme 5' terminal sequences of the parvovirus genome, wherein said viral proteins form empty parvovirus capsids within a transfected cell.

13. The DNA expression vector of claim 12, wherein the vector contains 65% of the parvovirus genome.

14. The DNA expression vector of claim 12, wherein the vector contains 83% of the parvovirus genome.

15. The DNA expression vector of claim 12, wherein the parvoviral capsids are canine, feline, mink, porcine, bovine or human parvoviral capsids.

* * * * *